United States Patent [19]

Bagnall

[11] 4,113,883

[45] Sep. 12, 1978

[54] ANAESTHETIC COMPOSITIONS

[75] Inventor: Robert David Bagnall, Runcorn, England

[73] Assignee: Imperial Chemical Industries Limited, London, England

[21] Appl. No.: 677,855

[22] Filed: Apr. 16, 1976

[30] Foreign Application Priority Data

Apr. 29, 1975 [GB] United Kingdom ............... 17698/75

[51] Int. Cl.² ............................................. A61K 31/08
[52] U.S. Cl. .................................................. 424/342
[58] Field of Search ......................................... 424/342

[56] References Cited

U.S. PATENT DOCUMENTS

| | | | |
|---|---|---|---|
| 3,769,433 | 10/1973 | Terrell | 424/342 |
| 3,769,434 | 10/1973 | Terrell | 424/342 |

*Primary Examiner*—Jerome D. Goldberg
*Attorney, Agent, or Firm*—Cushman, Darby & Cushman

[57] ABSTRACT

A pharmaceutical composition for use as an inhalation anaesthetic containing 1,2,2-trifluoroethyl difluoromethyl ether as active ingredient, and a method of using said ether to produce anaesthesia in a warm-blooded animal.

7 Claims, No Drawings

ANAESTHETIC COMPOSITIONS

This invention relates to a novel composition which possesses anaesthetic activity and which is substantially free from undesirable side-effects when administered to warm-blooded animals by inhalation.

According to the invention there is provided an anaesthetic composition which comprises as anaesthetic agent 1,2,2-trifluoroethyl difluoromethyl ether together with oxygen and optionally together with one or more other physiologically-acceptable material(s), the proportion of anaesthetic agent in the composition being such that when the composition is administered by inhalation to a warm-blooded animal anaesthesia is produced and/or maintained, and the proportion of oxygen in the composition being such that when the composition is administered by inhalation to a warm-blooded animal respiration is maintained.

The 1,2,2-trifluoroethyl difluoromethyl ether is a known compound (Tetrahedron, 1971, 27, 4533 to 4551), but it may most conveniently be obtained by the process described in our co-pending Application No. 50040/75. It is to be understood that the 1,2,2-trifluoroethyl difluoromethyl ether must be free of toxic impurities when it is used in the composition of the invention.

The oxygen present in the composition of the invention may be pure oxygen, or it may be in the form of air, that is in a mixture with nitrogen and smaller quantities of other gases.

The other physiologically-acceptable material(s) that may optionally be present in the composition of the invention may be, for example, one or more substances selected from other inhalant anaesthetics, for example halothane, nitrous oxide, diethyl ether, divinyl ether, trifluoroethyl vinyl ether, cyclopropane, trichloroethylene, chloroform, enflurane, fluroxene, methoxyflurane, teflurane and 1-chloro-2,2,2-trifluoroethyl difluoromethyl ether; pharmaceutically inert gases, for example nitrogen, chemically inert gases such as are present in air, for example neon, argon and xenon, and carbon dioxide and water vapour; and pharmaceutically-acceptable stabilisers which may be present to protect one or more of the other components of the composition from the effect of light, oxidation and/or attack by acid or base. As a suitable stabiliser there may be used, for example, a volatile stabilising agent which is physiologically tolerable, for example ethanol, or a non-volatile stabilising agent which is not carried over substantially during vaporisation, for example thymol.

The composition of the invention will usually contain between 0.25% and 10%, and more particularly between 0.5% and 6% volume by volume of the 1,2,2-trifluoroethyl difluoromethyl ether when used for induction of anaesthesia, and will usually contain between 0.25% and 3%, and more particularly about 2% when used for maintenance of anaesthesia.

The composition of the invention may be administered to warm-blooded animals, including man, for the production of anaesthesia by conventional techniques. The composition may be preformed and administered as such, or alternatively the 1,2,2-trifluoroethyl difluoromethyl ether and oxygen, either of which may have other physiologically-acceptable materials present with it, may be administered separately, the composition of the invention being formed either immediately prior to, or during, the course of administration. For example, the composition may be used in apparatus or machines adapted for the vaporisation of liquid anaesthetics and the admixture thereof with oxygen or with air or other gaseous mixtures containing oxygen in amounts capable of supporting respiration.

According to a further feature of the invention there is provided an inhalation anaesthetic apparatus charged with 1,2,2-trifluoroethyl difluoromethyl ether.

According to a further feature of the invention there is provided a method for producing anaesthesia in a warm-blooded animal which comprises administering to said animal an anaesthetically-effective amount of 1,2,2-trifluoroethyl difluoromethyl ether together with sufficient oxygen to maintain respiration.

The invention is illustrated but not limited by the following Examples:

EXAMPLE 1

A group of 6 mice is placed in a chamber of 10 liters capacity which contains solid soda lime, and a mixture of difluoromethyl 1,2,2-trifluoroethyl ether and oxygen, of known percentage, is released into the chamber. A reservoir bag containing the known percentage mixture is used to maintain atmospheric pressure as the mixture is inhaled by the mice and as exhaled carbon dioxide is absorbed by the soda lime. After 30 minutes the concentration of difluoromethyl 1,2,2-trifluoroethyl ether in the chamber is determined by gas chromatography.

The experiment is repeated using different mixtures of difluoromethyl 1,2,2-trifluoroethyl ether and oxygen, and the $AC_{50}$, that is the concentration by volume of difluoromethyl 1,2,2-trifluoroethyl ether which anaesthetises 3 mice out of 6 after 30 minutes exposure, is found to be 1.35%. The $LC_{50}$, that is the concentration by volume of difluoromethyl 1,2,2-trifluoroethyl ether which kills 3 mice out of 6 after 30 minutes exposure, is found to be 7.0%. The therapeutic ratio of the compound is therefore 7.0/1.35, that is 5.2. Under similar conditions the $AC_{50}$, $LC_{50}$ and therapeutic ratio for halothane are respectively 0.85%, 3.4% and 4.0.

EXAMPLE 2

A cat is anaesthetised with thiopentone sodium and a polyethylene cannula is inserted into a femoral artery to enable arterial blood pressure (b.p.) to be measured and to enable samples of arterial blood to be collected for measurement of the partial pressure of carbon dioxide ($pCO_2$) therein. Various mixtures of difluoromethyl 1,2,2-trifluoroethyl ether and oxygen are delivered to the cat by means of an Ayres T-piece and an endotracheal tube, and the arterial b.p. and $pCO_2$ are measured for each of the mixtures. The experiment is then repeated in each of three further cats, and the mean b.p. and $pCO_2$ is calculated for each mixture. These mean values are shown in the following table. It is found that the minimum concentration of the ether in oxygen which maintains anaesthesia in the cat is 2% volume by volume.

| % (v/v) ether in oxygen | arterial b.p. (mm.Hg.) | arterial $pCO_2$ (mm.Hg.) |
| --- | --- | --- |
| 2 | 107 | 32.6 |
| 3 | 79 | 36.5 |
| 4 | 64 | 42.4 |

Under similar conditions the minimum concentration of halothane in oxygen which maintains anaesthesia is 1% volume by volume, and the following mean arterial b.p. and pCO₂ values are found with varying concentrations of halothane in oxygen.

| % (v/v) halothane in oxygen | arterial b.p. (mm.Hg.) | arterial pCO$_2$ (mm.Hg.) |
|---|---|---|
| 1 | 70 | 29.4 |
| 1.5 | 60 | 34.9 |
| 2 | 57 | 44.5 |

It will be seen that difluoromethyl 1,2,2-trifluoroethyl ether is less hypotensive than halothane at comparable anaesthetic concentrations, and that pCO$_2$ measurements show there to be no significant difference between the respiratory depressant effects of difluoromethyl 1,2,2-trifluoroethyl ether and halothane.

EXAMPLE 3

A cat is prepared as described in Example 2, and additionally a polyethylene cannula is inserted into a femoral vein to enable infusion of adrenaline, and the cat's heart is monitored by electrocardiogram. The cat is then maintained under anaesthesia with a 2% v/v mixture of difluoromethyl 1,2,2-trifluoroethyl ether and oxygen, and increasing amounts of adrenaline are infused until a ventricular arrhythmia occurs. The experiment is repeated in each of three further cats and the mean minimal arrhythmic dose of adrenaline is found to be 8.07 ug./kg. bodyweight.

Under similar conditions the mean minimal arrhythmic dose of adrenaline when cats are anaesthetised with 1% v/v halothane and oxygen is found to be 2.83 ug./kg. bodyweight. It will be seen, therefore, that difluoromethyl 1,2,2-trifluoroethyl ether causes less sensitivity of the heart to adrenaline than does halothane.

What we claim is:

1. An anaesthetic composition which comprises as an anaesthetic agent 1,2,2-trifluoroethyl difluoromethyl ether which is admixed with oxygen, wherein the amount of anaesthetic agent in the composition is anaesthetically effective when the composition is administered by inhalation to a warm-blooded animal, and wherein the amount of oxygen in the composition is effective to maintain respiration in said animal when the composition is administered by inhalation.

2. A composition as claimed in claim 1 which includes a physiologically-acceptable material selected from the group consisting of other inhalant anaesthetics, pharmaceutically inert gases, chemically inert gases present in air, carbon dioxide, water vapour; and pharmaceutically-acceptable stabilisers.

3. A composition as claimed in claim 1 which contains between 0.25% and 10% volume by volume of the 1,2,2-trifluoroethyl difluoromethyl ether.

4. A composition as claimed in claim 3 which contains between 0.5% and 6% volume by volume of the 1,2,2-trifluoro-ethyl difluoromethyl ether.

5. A composition as claimed in claim 1 which contains between 0.25% and 3% volume by volume of the difluoromethyl 1,2,2-trifluoroethyl ether.

6. A composition as claimed in claim 5 which contains 2% volume by volume of the difluoromethyl 1,2,2-trifluoroethyl ether.

7. A method for producing anaesthesia in a warm-blooded animal which comprises administering by inhalation to said animal an anaesthetically-effective amount of 1,2,2-trifluoroethyl difluoromethyl ether together with sufficient oxygen to maintain respiration.

* * * * *